United States Patent
Enk

(10) Patent No.: US 6,485,428 B1
(45) Date of Patent: Nov. 26, 2002

(54) APPARATUS FOR AND METHOD OF INTRAVASAL PRESSURE MEASUREMENT AND LOW-CONTAMINATION INSERTION OF CATHETERS FOR EXAMPLE INTO BLOOD VESSELS

(76) Inventor: Dietmar Enk, Stadtbusch 35, D-48653 Coesfeld (DE)

(*) Notice: Subject to any disclaimer, the term of this patent is extended or adjusted under 35 U.S.C. 154(b) by 0 days.

(21) Appl. No.: 09/673,988

(22) PCT Filed: Apr. 21, 1999

(86) PCT No.: PCT/EP99/02689

§ 371 (c)(1),
(2), (4) Date: Jan. 2, 2001

(87) PCT Pub. No.: WO99/53835

PCT Pub. Date: Oct. 28, 1999

(30) Foreign Application Priority Data

Apr. 21, 1998 (DE) .......................................... 198 17 762

(51) Int. Cl.[7] .................................................. A61B 5/02
(52) U.S. Cl. .................... 600/487; 600/485; 600/486; 600/561; 600/576; 600/578; 600/579
(58) Field of Search .................. 600/485–488, 600/561, 576–579; 604/38, 121, 118, 218, 311; 73/744, 747

(56) References Cited

U.S. PATENT DOCUMENTS

| | | | | |
|---|---|---|---|---|
| 2,866,453 A | * | 12/1958 | Jewett | 600/487 |
| 3,656,480 A | * | 4/1972 | Rubricius | 604/218 |
| 3,730,168 A | * | 5/1973 | McWhorter | 600/560 |
| 3,807,389 A | * | 4/1974 | Miller et al. | 600/487 |
| 3,942,514 A | * | 3/1976 | Ogle | 600/577 |
| 4,282,881 A | | 8/1981 | Todd et al. | |
| 4,624,659 A | * | 11/1986 | Goldberg et al. | 604/121 |
| 4,727,887 A | * | 3/1988 | Haber | 600/561 |
| 4,759,750 A | * | 7/1988 | DeVries et al. | 604/121 |
| 4,813,938 A | | 3/1989 | Raulerson | |
| 4,817,629 A | | 4/1989 | Davis et al. | |
| 5,106,371 A | * | 4/1992 | Zhao et al. | 604/110 |
| 5,314,415 A | * | 5/1994 | Liebert et al. | 604/218 |
| 6,086,559 A | * | 7/2000 | Enk | 604/121 |

FOREIGN PATENT DOCUMENTS

FR 2 286 536 11/1975

* cited by examiner

Primary Examiner—Robert L. Nasser
Assistant Examiner—Patricia C. Mallari
(74) Attorney, Agent, or Firm—Laurence A. Greenberg; Werner H. Stemer; Ralph E. Locher

(57) ABSTRACT

The invention concerns a one-person-operable, sterilisable, medical pressure measuring apparatus (1: 6: 8: 11: 12: 23: 31), in particular for blood pressure measurement, wherein the pressure measuring apparatus (1: 8: 11: 12: 23: 31) has least one cannula connection (26), a measuring duct (4) and an entry (27). The measuring duct (4) opens into a closed container (2) with rigid walls (7), a compressible medium (3) being disposed in the container (2). The pressure measuring apparatus (1: 6: 3: 11: 12: 23: 31), besides the measurement of the pressure in a vessel, permits contamination-free insertion of a catheter, preferably for monitoring the position of a cannula (24). Unnecessary injury to vessels can be avoided thereby and complications upon the insertion of catheters can be considerably reduced.

41 Claims, 7 Drawing Sheets

APPARATUS FOR AND METHOD OF INTRAVASAL PRESSURE MEASUREMENT AND LOW-CONTAMINATION INSERTION OF CATHETERS FOR EXAMPLE INTO BLOOD VESSELS

BACKGROUND OF THE INVENTION

Field of the Invention

Central-venous catheters, that is to say catheters which are inserted into large veins near to the heart, are used for the measurement of given haemodynamic parameters and for the continuous or discontinuous application of medicaments or infusion solutions and are an important component of patient monitoring and (intensive) medical care. The puncturing or aspiration of veins which are near to the heart presupposes skill, experience and knowledge of the anatomical factors involved. Besides the variability of the position of veins near to the heart in particular difficult puncturing conditions repeatedly result in incorrect puncturing of arteries which are in adjacent relationship.

Arterial puncturings or aspirations with thick cannulae as are used for the insertion of guide wires or catheters can result in massive bleedings under pressure into the surrounding tissue for example nerves, and then necessitate operative rectifying intervention. Incorrect arterial puncturing can represent a considerable risk to a patient who must undergo an operative procedure using a heart-and-lung machine and whose blood is made non-coagulatable for that purpose. Puncturing a vessel wall which has been arteriosclerotically altered can result in the mobilisation of plaques which are entrained with the blood flow into smaller arteries and can clog same. For that reason incorrect arterial puncturing in the region of the vessels in the neck which also supply the brain (arteria carotes) can result in a stroke and possibly disability of a patient. Those complications, even if rare, which however are tragic in the individual situation in which they occur and which involve high consequential costs have resulted in the recommendation of firstly finding veins which are close to the heart, by means of a thin needle (pre-puncturing cannula or also referred to as a "finder-needle") in order then to puncture the vessel with the thicker cannula, in the direction of puncturing of the finder-needle.

In the arteries of the circulatory system of the body a mean pressure of 70–100 mm Hg with an amplitude between systolic and diastolic pressure of about 40–60 mm Hg is physiological, whereas in the veins which are close to the hear of the circulatory system a mean pressure of 7–10 mm Hg with an amplitude of only a few mm Hg is physiological. Under pathological conditions the pressure difference between arteries and veins and also the pressure amplitude in the vessels can become both greater and also smaller.

If an artery is punctured with a cannula having a large lumen, that can generally be recognised by virtue of the spraying and pulsating discharge of blood from the cannula. In contrast after a vein is punctured the blood will flow away from the cannula under a low pressure and fairly continuously Irrespective of whether an artery or a vein has been punctured however the high through-flow resistance of cannulae with a small lumen results in a uniform discharge of blood from the cannula, which at most pulsates discretely and never sprays out. Accordingly recourse must be had to other criteria in order to identify an artery or a vein. The colour of the blood is therefore a poor criterion.

By virtue of the higher oxygen content arterial blood is normally lighter than venous blood. Lung or heart diseases however can have the result that arterial blood also appears comparatively dark: in contrast venous blood is also really light when the patient is breathing with pure oxygen, for example in the context of initiating anaesthesia.

A reliable possible way of distinguishing arterial and venous blood is blood gas analysis in which the oxygen and carbon dioxide partial pressures are measured. That is time-intensive and labour-intensive and thus expensive.

The blood pressure in the punctured vessel can also be measured directly by means of a riser line. When the blood is allowed to flow back into the line the transfer of several milliliters of blood into the line requires some time, depending on the through-flow resistance of the cannula. If in contrast operation is conducted with a riser line which is filled with liquid, for example filled with common salt solution preparation of the riser line is a comparatively time-consuming procedure. At any event an assistant is required in order to hold the riser line.

A pressure-converter system, which is referred to as a transducer system, again detects not only the mean blood pressure as with a riser line but also the blood pressure amplitude in the punctured vessel. As the insertion of catheters presupposes sterile operating conditions, this procedure necessarily means that the transducer system must firstly be prepared in a sterile condition, that is highly time-consuming and also requires a "third hand" to which the cable connection for connection to the monitor can be handed over.

In view of the level of expenditure and complication and the difficulties involved in identifying a vein which is close to the heart without any doubt by means of a feeder-needle clinical practice often involves foregoing the pre-puncturing procedure. Unintentional arterial puncturings are then only detected after insertion of the catheter by means of intravasal pressure measurement or by virtue of blood rising in the infusion system and/or by an X-ray of the thorax.

The risk of HIV- (AIDS-) or hepatitis infection by virtue of contact with the blood of infected patients has resulted in "closed" cannula or syringe systems being offered not only for taking blood but also for the insertion of central-venous or arterial catheters. A closed system for example for the pressure-controlled handling of a fluid is known from the present applicant's DE 195 03 230.

So-called side-port cannulae are in turn available on the market for the low-contamination insertion of central-venous catheters. They have an additional duct which is disposed laterally and which is closed by a valve mechanism and by way of which a guide wire can be introduced after puncturing of the vessel, by way of which wire the catheter is then pushed into the vessel: the so-called "Seldinger procedure". Furthermore, a syringe is also known from U.S. Pat. No. 4,813,938, referred to hereinafter as the "Raulerson syringe", with a through duct in the plunger, which is closed by a valve mechanism and through which a guide wire can be introduced into the punctured vessel without the syringe having to be disconnected.

Both systems effectively prevent the escape of blood even after unintentional puncturing of an artery with a cannula having a large lumen, and accordingly give a false sense of security. As the syringe and the cannula do not have to be disconnected, as in the conventional procedure, incorrect arterial puncturing is usually recognised only after insertion of the catheter and thus maximum trauma for the vessel wall.

The object of the present invention is to provide a compact apparatus which is simple to operate and which can measure the pressure in a cavity, and which in particular permits a precise reliable distinction to be drawn between veins and arteries by means of a cannula, wherein the apparatus permits controlled insertion of a catheter or the like, in such a way as to avoid unnecessary injuries, in particular with the exclusion of blood contamination of the person operating the apparatus.

A first configuration of the invention is a one-person-operable, sterilisable, medical pressure measuring apparatus or manometer which has at least one cannula connection, a measuring duct and an entry, and wherein the measuring duct opens into a closed container with rigid wells in which there is a compressible medium.

Therefore, a liquid does not rise against the force of gravity, as in the case of the known construction, in an open container, for example a riser line, but penetrates into a closed container of a given volume and with non-elastic walls, which is for example filled with air, and in so doing successively compresses the air.

The pressure resulting in a closed container of that nature is now calculated from the quotient of the uncompressed volume of air and the volume of air compressed by the liquid which has passed into the container, and is dependent on the specific weight of the entering liquid: if for example 6 ml of uncompressed air is compressed to 5 ml, that gives a pressure of 1.2 bar (=about 910 mm Hg or about 1210 cm head of water) or a pressure above atmospheric of 0.2 bar (=about 150 mm Hg or about 200 cm. head of water).

As is internationally further usual in medical linguistic usage or for reasons of greater clarity reference will be made hereinafter to the pressure units "bar". "mm Hg" or "cm head of water".

By means of that calculation a given pressure can be associated with a given level of liquid in the container and in that way it is possible to calibrate a scale on which the pressure of the compressed air can be directly read off with the column of liquid as a pointer. Having regard to the hydrostatic pressure of the column of liquid which also involves the specific weight of the liquid it is also possible to specify the pressure under which the liquid is. If the liquid is for example "a physiological" common salt solution with a specific weight of about 1 then the error resulting from a column of liquid of a few centimeters can be disregarded for the measurement of arterial blood pressures.

In a handy pressure measuring apparatus which is also suitable for the measurement of central-venous and arterial mean pressures, connected upstream of the container is the measuring duct which is also of a predetermined volume and also has non-elastic walls for completely receiving the rising liquid, which is either outside or inside the container. In that case, the quotient of the volume of air in the measuring duct to the total volume of air in the measuring duct and the container gives the measuring range over which the pressure can be comparatively accurately read off at the level of liquid in the measuring duct: for example on a measuring duct which accommodates 1 ml of the pressure measuring apparatus with a total air volume of 6 ml, it is possible to read off pressures above atmospheric of between 0 and about 150 mm Hg and thus also the pathologically increased arterial mean pressures of a patient with high blood pressure. A lower ratio between the volume of air in the measuring duct and the total air volume in the measuring duct and container admittedly increases the measuring range but worsens the degree of reading accuracy.

As even when the measuring duct involves a diameter of 3 mm the surface tension of the liquid prevents the liquid passing into the measuring duct due to the force of gravity, the pressure measuring apparatus can be arranged in such a way that the measuring duct extends horizontally and thus the hydrostatic pressure of the column of liquid no longer causes any measurement errors.

Due to the principle involves, such a pressure measuring apparatus measures more accurately in a situation involving only slight compression of the volume of air contained therein, than when a greater degree of compression is involved. The level of measuring accuracy for low pressures can be very easily further improved by means of a measuring duct of different cross-sections (with a cross-section which is smaller close to the cannula and larger towards the container).

The above-described pressure measuring apparatus is now fitted between the cannula and the syringe before the commencement of the puncturing operation. That blood pressure measuring apparatus may however first be "connected in parallel" (=opened) for blood pressure measurement (for example by means of a three-way tap) if blood can be slightly aspirated (=sucked into the syringe cylinder). Otherwise (in spite of the aspiration being "damped" by the volume of air of a "parallel-connected" blood pressure measuring apparatus) air can be sucked out of the blood pressure measuring apparatus into the syringe cylinder, whereby the apparatus loses its calibration and incorrectly high blood pressure values are measured.

The blood pressure can be measured either by blood being allowed to pass under the blood pressure in the punctured vessel into the measuring duct or by a procedure whereby blood is passed under pressure into the measuring duct by injection and then the operator waits for the drop in the column of blood until pressure equalisation occurs. As in both cases only a small volume of blood has to pass into or out of the blood pressure measuring apparatus, in contrast to measuring pressure with a riser line, the blood pressure can be measured very quickly.

The contamination problem is resolved by the cannulae being closed, for example by means of a three-way tap, prior to disconnection of the syringe, and being opened again only for the advance of the guide wire for a catheter or of the catheter itself.

The described pressure measuring apparatus can also advantageously be used on so-called side-port cannulae, as are described above. The attachment of the pressure measuring apparatus only has to be designed in such a way that, by fitting onto the side port, the valve mechanism disposed there is overcome and, after disconnection, closes again (in order then to be able to introduce the guide wire under low-contamination conditions). It is to be observed that some air is generally disposed in the side port of such cannulae, and in the pressure measurement operation that air can result in an incorrectly low pressure indication if that additional volume of air is not taken into consideration when calibrating the scale of the pressure measuring apparatus.

The syringe described in above-mentioned DE 195 03 230, to the disclosure of which reference is directed here in this respect in terms of the full content thereof, is also suitable for blood pressure measurement by means of cannulae having a small lumen. In this so-called "Enk syringe" the container and the measuring duct in the container are disposed in the plunger of the syringe An advantage of this syringe is that upon venting of the syringe cylinder a pressure measuring apparatus of that syringe is always equalised in relation to ambient air pressure, being what is known as "zeroed", and remains calibrated, as the air in the pressure measuring apparatus of the syringe is only in contact with the liquid, which is also at room temperature, for example common salt solution, in the syringe cylinder, and is not directly in contact with blood at body temperature.

The syringe makes it possible for the entire "measuring limb" to be flushed out of the syringe cylinder by the injection of liquid, for example common salt solution. In that situation liquid is passed into the measuring duct under pressure at the same time. As the friction of the sealing lip always holds the plunger in its position in the syringe cylinder, even when completely relieved of load by the injecting finger, the syringe now injects under decompression of the air in the plunger until the pressure corresponds to the vessel pressure. As in that case the cannula is continually being flushed coagulating blood cannot clog and block the cannula and the vessel wall is always pressed away from the cannula.

The blood pressure can also be measured with such a syringe for example by means of so-called side-port cannulae. The problem of the loss of air from the pressure measuring apparatus of that liquid-filled syringe due to aspiration with the conventional syringe does not arise in that case as the pressure measuring syringe is only connected to the side-port for the blood pressure measurement operation, possibly by way of an adaptor which lifts open the valve mechanism.

A measuring duct of a cross-section which is smaller in the front portion and larger in the rear portion improves the accuracy and readability of the pressure measuring apparatus (=syringe with a low- and high-pressure measuring range): the (mean) pressure of central veins can be accurately measured in the front, long measuring passage portion having a small lumen. Due to the magnifying lens effect of the thick cannula wall the level of liquid or the scale in that region can be clearly seen even if the plunger is pushed into the syringe cylinder. The higher arterial (mean) pressures are measured in the rear, short measuring duct portion having the large lumen, even if such measurement is somewhat less accurate. As that region of the plunger projects out of the syringe cylinder the level of liquid can always be read off here without any problem.

The following calculation by way of example is intended to illustrate this: let there be a plunger with a total air volume of 8 ml: in that case 0.8 ml is apportioned to the measuring duct. If now the measuring duct is completely filled with liquid compression of the volume of air from 8 ml to 7.2 ml corresponds to a pressure above atmospheric of about 0.11 bar (=about 84 mm Hg) with a length of 50 mm and an inside diameter of 2 mm the front measuring duct portion is of a volume of about 0.157 mm corresponding to a measuring range of between 0 and about 0.02 bar (=about 15 mm Hg) pressure above atmospheric. The rear measuring duct portion is of a length of 32.8 mm and is of an inside diameter of 5 mm: that results in a volume of about 0.644 ml and a measuring range of between 0.02 and about 0.11 bar pressure above atmospheric.

In a further configuration the measuring duct can also become continuously larger from the inside diameter.

Another possible way of adapting the pressure measuring apparatus to different pressure measuring ranges is afforded by a closure portion with which the air volume of the plunger, which communicates with the syringe cylinder, can be selectively reduced or increased in size (for example with a closure portion which is displaceable in the plunger and which selectively closes the rear opening of the measuring duct or even parts thereof). In that arrangement a screw mechanism or a bayonet arresting means always holds the closure portion in the defined position in the plunger and thus ensures pressure measuring accuracy.

If a suitable closure or valve mechanism in the closure portion or however the wall of the plunger makes it possible for the cavity in the plunger to be selectively opened for pressure equalisation relative to the ambient air, then a pressure measuring apparatus of that kind can also be used to measure negative pressures on a suitably calibrated scale, for example the pressure below atmospheric which occurs due to aspiration. that is to say by withdrawing the plunger in the syringe cylinder: after the liquid is drawn up into the syringe cylinder the plunger is opened to atmospheric pressure, for example by means of a slider or two openings which are rotatable relative to each other in the wall of the plunger and the closure portion. After some liquid has been urged into the measuring duct as far as a zero marking, for example half of the measuring duct, when the outlet opening of the syringe cylinder is closed, by virtue of a forward displacement movement of the plunger, for example by slowly "screwing in" the plunger by means of a screwthread in the syringe cylinder and on the plunger, the plunger is air-tightly closed off again in relation to atmospheric pressure. Now positive and also negative pressures can be measured. That option is also afforded by a closure portion which is displaceable in the plunger: after liquid has been drawn up into the syringe cylinder and the syringe cylinder has been vented, the closure portion is pulled back or turned back in the plunger until the liquid which is passing into the measuring duct has reached the zero marking.

As a particularly desirable configuration of a pressure measuring apparatus. described hereinafter is a system having a syringe with which it is not only possible to implement an aspiration procedure, but also the pressure in the punctured vessel or liquid cavity can be measured and through which a guide wire for a catheter or a catheter itself can subsequently be pushed for example into a blood vessel, without the syringe having to be disconnected from the cannula.

The syringe has a syringe cylinder and a hollow plunger with a damping and pressure measuring device corresponding to the "Enk syringe". At the rear the plunger has a closure portion with a bore therethrough, which can be opened or closed by a sliding or rotating mechanism or a valve mechanism which is known for example from the "Raulerson syringe", and through which for example a guide wire for a catheter or a catheter itself can be moved forwardly into the duct of the pressure measuring device. If the duct additionally has at least one sufficiently large lateral opening the duct of the pressure measuring device can also be accommodated by the closure portion in the sense of a centering effect.

The handling of that syringe is described hereinafter by reference to the example of puncturing a blood vessel and inserting a guide wire for a catheter into the vessel:

By retraction of the plunger, a pressure below atmospheric which is "damped" in comparison with a normal syringe also occurs in the syringe cylinder of this syringe: liquid, for example common salt solution can be drawn up or raised into the syringe cylinder by the reduced pressure, against the force of gravity. In that procedure the syringe must be held with its cannula attachment downwardly and there should be some air in the syringe cylinder, about 1 ml. Otherwise liquid can penetrate into the duct due to the pressure below atmospheric which also obtains in the plunger, particularly in the case of a strong aspiration effect. A bar which is disposed at the end of the plunger projecting out of the syringe cylinder and which fits into a corresponding opening in the syringe cylinder only in a given rotational position ensures that the plunger cannot be accidentally entirely pushed into the syringe cylinder.

The syringe is now vented conventionally, that is to say held with the cannula attachment up, and the air is dispelled from the syringe cylinder by moving the plunger forwardly. When that happens the liquid closes the front opening of the duct. Even with a duct opening of three millimeters the surface tension of the liquid prevents liquid from penetrating into the duct due to the force of gravity. When venting the syringe the air in the plunger is closed off from the surrounding atmosphere and thereby the pressure measuring device is "zeroed" (=calibrated to zero).

In the attempt to puncture a blood vessel with the cannula fitted onto the syringe, it is never possible to aspirate as extremely as with a conventional syringe as the air in the plunger also "damps" the aspiration effect. This can prevent punctured veins from collapsing or the cannula from being sucked against the vessel wall, as is otherwise possible in she event of a strong aspiration effect. As no blood is to be aspirated in those situations, it is erroneously assumed that the blood vessel has not yet been reached or has already been left again. That causes an increase in the number of incorrect or multiple puncturings. Accordingly a "damped" aspiration effect can certainly be advantageous.

If a blood vessel is punctured, as can be seen from the sudden entry of blood into the syringe cylinder, the liquid in the syringe cylinder acts as a highly effective buffer. Even in the event of a strong aspiration effect, that prevents the blood-liquid mix from being sucked directly into the duct, and thus prevents the pressure measuring device from losing its calibration. In addition the blood is immediately diluted by the liquid and thus cannot coagulate in the syringe. Admittedly a slight increase in temperature and thus expansion of the air also occurs, with the passage of time, by virtue of mixing of the liquid at ambient temperature with the blood which is at body temperature. As however the blood pressure is now measured directly, the resulting measurement error (wrongly low values) is also negligible having regard to the pressure difference to be detected as between veins and arteries.

For blood pressure measurement in the punctured vessel, the plunger is now advanced somewhat. As a result the blood-liquid mix is partially injected and partially urged into the duct. As the plunger always retains its position in the syringe cylinder due to a sufficiently high level of friction of the sealing lip, even if the finger which is advancing the plunger completely relieves the load thereon, the blood pressure of the punctured vessel can be read off, for example at a calibrated scale in or on the plunger, as soon as the level of liquid in the duct is no longer moving.

The "coloured" column of the blood-liquid mix as a "pointer" of the pressure measuring device is easily visible. However even a column of clear liquid can be clearly seen in the duct by virtue of neutralisation of the birefringence effect of the duct wall.

Alternatively it is also possible to operate with a syringe which is prepared for the measurement of negative pressures (see above): after the puncturing cannula has been inserted the plunger is withdrawn in the syringe cylinder until the desired pressure below atmospheric is attained. With a suitable design in respect of the circular sealing lip of the plunger, the plunger is in that case again held in its position in the syringe cylinder and thus the set reduced pressure is maintained. When the cannula punctures a blood vessel, the level of liquid in the duct rises abruptly until pressure equalisation with the pressure in the vessel occurs.

If measurement of the blood pressure shows they the desired vessel, for example a vein, has been punctured, the plunger is pushed completely into the syringe cylinder and thereafter the guide wire for the catheter or the catheter Itself is pushed into the blood vessel through the closure portion, the measuring duct, the cannula attachment of the syringe cylinder and the cannula fitted thereon. In that situation the blood-liquid mix is injected. If by mistake the measuring duct is "over-injected" due to very rapid injection, the blood-liquid mix drips into the cavity of the plunger and is "enclosed" there. Contamination of the working area is avoided in that way. As however an increased pressure can thus be built up in the plunger, pass due to the air out of the plunger into the syringe cylinder and be injected due to inattentiveness. "over-injection" of the duct should be avoided.

Injection of the blood-liquid mixture does not represent a danger from the point of view of the patient: admittedly, activation of coagulation of the aspirated blood may occur due to the contact with a foreign surface. However the coagulation factors are immediately severely diluted by the liquid in the syringe cylinder. The blood cannot therefore "clot" and a blood clot will never be injected.

In principle it is necessary to operate with such a syringe "from above downwardly", that is to say the cannula attachment on the syringe is the lowest point and the end of the plunger is the highest. That corresponds to the working situation when puncturing the vena jugularis irterna, which is the central-venous entry that is in fact most frequently used, and the vena femoralis. Admittedly, in an aspiration situation air passes out of the plunger into the syringe cylinder but that air is "captured" again in quantitative terms after puncturing of a blood vessel with the penetration of liquid into the syringe cylinder or in the forward movement of the plunger. If in contrast operation is effected "from below upwardly" air is permanently lost from the plunger and there is the danger of mistakenly injecting the air which has passed into the syringe cylinder, in that case also liquid is sucked into the measuring duct due to the reducer pressure in the plunger and the pressure measuring device is mis-calibrated as a result.

Even when working correctly a small air bubble remains in the angle between the syringe cylinder and the front face of the plunger. The mis-calibration (wrongly high pressure indication) resulting from that remaining loss of air from the pressure measuring device into the injection cylinder becomes progressively smaller with the same lost volume with an increasing air volume in the plunger. As when inserting catheters into blood vessels it is the difference between venous and arterial pressure hat is being considered, and thus a pressure difference of at least 50 mm Hg or about 65 cm water head, that error is scarcely relevant. If the procedure adopted is such that the cannula fitted onto the cannula attachment is not vented prior to the puncturing operation, then the air in the cannula completely compensates for the calibration error if the volume corresponds to the loss from the plunger.

The air which has passed into the syringe cylinder upon aspiration can also be completely "captured" again by means of a plunger front face which is shaped concavely towards the opening of the measuring duct if, as described above, operation is implemented with the syringe "from above downwardly". In that case however the cannula must be vented, otherwise the air in the cannula can again cause a small calibration error (wrongly low pressure indication).

If now the measuring duct is arranged not centrally but eccentrically in the plunger, the measuring duct can be closed prior to aspiration by rotation of the plunger relative to the sealing lip. The plunger is first rotated again for pressure measurement and for subsequent insertion of a guide wire or catheter, in such a way that a opening in the sealing lip comes into alignment with the measuring duct.

The sealing lip can be easily prevented from also rotating by virtue of a thickening in the wall, for example a bar, at the inside wall of the injection cylinder and a corresponding opening in the sealing lip. The thickening in the wall which acts like a magnifying lens improves the perceptibility of the pressure indication which does not have to be read off through three layers of plastic material, as in the case of a measuring duct which is disposed centrally in the plunger, but possibly only through two layers of plastic material.

By virtue of two mutually oppositely disposed spherical thickenings of the sealing lip the correct rotational position of the plunger for closure or opening respectively of the pressure measuring device can be easily detected: the double seal which "latches" into the lumen of the measuring duct reliably closes off the air volume in the plunger upon aspiration, relative to the exterior. The air of the pressure measuring device cannot in that way escape from the plunger even in the event of strong aspiration which in this case is "undamped".

The rotational position, which is necessary for pressure measurement or for advance movement of the guide wire or catheter and which also involves a "latching" effect, of the plunger relative to the sealing lip and relative to the cannula attachment of the syringe cylinder, which is also disposed in eccentric relationship, is in contrast afforded when a mark on the plunger is brought into alignment with a mark on the syringe cylinder and thus for example the eccentrically disposed measuring duct is directly under he thickening of the wall of the syringe cylinder.

Air-tight closure of the pressure measuring device can also be achieved by means of a circular sealing lip of variable depth, which lies in a circular groove in the plunger of also variable depth: depending on the rotational position of the plunger the sealing lip is squashed together to a greater or lesser degree and thereby an opening in the sealing lip is selectively opened or closed. The friction of the sealing lip can also be varied in that way as desired.

A comparable mechanism in the closure portion of the plunger serves to open the plunger after pressure measurement has been effected for introducing the guide wire or catheter.

If the measuring duct does not have at least one large, laterally disposed opening to the cavity of the plunger, the bore in the closure portion should not form a through communication with the measuring duct: on the one hand a gap between the measuring duct and the closure portion does not cause a problem in the forward movement of the guide wire or the catheter. On the other hand it is crucial for correct functioning of the pressure measuring device and like a laterally disposed opening ensures that even after arterial puncturing upon opening of the bore in the closure portion blood can at most drip out of the measuring duct into the cavity of the plunger. In the case of a bore which passes through the entire plunger in contrast only a valve mechanism which is more complicated from the point of view of structure and production procedure and which is thus more expensive prevents blood from issuing from the syringe.

With that syringe it is not absolutely necessary to operate "from above downwardly": as the pressure measuring device in the plunger is closed after preparation of the syringe (drawing up liquid, venting the syringe) and is opened for the pressure measurement procedure only after puncturing of a blood vessel has been effected, no air is "lost" from the piston in the aspiration operation and therefore also does not need to be "captured" again.

In contrast to the above-described configurations of the invention it is therefore possible with this syringe also to operate "from below upwardly", as is often necessary in operations for puncturing the vena subclavia. In addition aspiration is effected with this syringe as with a conventional syringe in an "undamped" mode.

After the correct cannula position has been secured by means of blood pressure measurement the plunger is pushed entirely into the syringe cylinder again in order subsequently to be able to advance the guide wire or catheter through the syringe into the blood vessel. If in that situation there is a wish to avoid completely injecting the blood-liquid mix, the bore in the closure portion can already be opened prior to the forward movement of the plunger: the blood-liquid mix is now partially injected into the cavity of the plunger. When that happens the air escapes from the plunger through the bore in the closure portion. Accordingly a pressure above atmospheric does not build up in the plunger and air cannot therefore possibly pass into the syringe cylinder.

A further possible way of switching off the pressure measuring device of the syringe in the aspiration operation is afforded by a mandrel or bar portion which sealingly closes the front opening of the measuring duct. That bar portion is only withdrawn from the measuring duct when pressure is to be measured or inserted again when aspiration is to be implemented once more. This construction requires a valve mechanism in the closure portion. In this construction the front opening of the measuring duct should be of a smaller cross-section than the measuring duct itself, otherwise the bar portion in the measuring duct can behave like a plunger and upon being withdrawn suck liquid into the measuring duct.

Withdrawal of the bar portion results in a calibration error: the volume of the bar portion is suddenly missing and causes a minimal pressure below atmospheric in the pressure measuring device, with the consequence of a wrongly high pressure indication. If the bar portion is of a suitably small volume however the calibration error can be disregarded or can be taken into consideration when calibrating the scale from the outset.

If the bar portion is already completely pulled out of the plunger for the pressure measurement operation, as is necessary for advancing the guide wire or catheter, the calibration error can also be minimised in the following way, if the valve mechanism in the closure portion of the plunger is of a suitable design configuration: if when the bar portion is pulled out the function of the valve mechanism is neutralised for a brief moment, the pressure of the air in the pressure measuring device becomes equal to the ambient air pressure ("zeroing") It is to be noted in that respect that, if the valve function is neutralised for an excessively long period of time, due to the blood-liquid mix penetrating into the measuring duct, too much air can also escape from the pressure measuring device and the calibration error is increased in that way (incorrectly high pressure indication). This variant of the syringe can also be operated. "from below upwardly" and aspiration can also be effected in an "undamped" manner.

In the case of a syringe which is also prepared for the measurement of negative pressures and in which the pressure measuring device is for example correctly "zeroed" with a half-filled measuring duct, the problem of a loss of air from the pressure measuring device into the syringe cylinder occurs only to a limited degree. As long as aspiration is not effected to a greater extent than is detected by the measuring range of the syringe, no air is "lost".

A problem which in principle is greater, in regard to mis-calibration of the pressure measuring device, arises in connection with sucking in air in the case of a cannula which is not air-tightly fitted onto the cannula attachment (incorrectly low pressure indication). Due to the principle involved in such a case the syringe has to be vented afresh on each occasion.

Further advantageous configurations and developments and features of the invention are described in greater detail in the following specific description. In the drawing:

For the sake of simplification in the specific description hereinafter similar components are denoted by the same references.

DESCRIPTION OF THE PREFERRED EMBODIMENT

Figure 1:
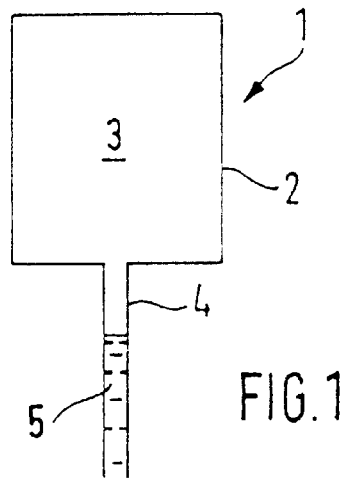
FIG. 1 shows a first pressure measuring apparatus with a container and a measuring duct.

FIG. 1 shows a first pressure measuring apparatus 1 with a closed container 2. A compressible medium 3 is disposed in the container 2. A measuring duct 4 opens into the container 2. The measuring duct 4 is at least partially filled for example with a common salt solution 5. The measuring duct 4 serves as a riser line. A visible height of the common salt solution 5 or of blood indicates the pressure applied.

Figure 2:
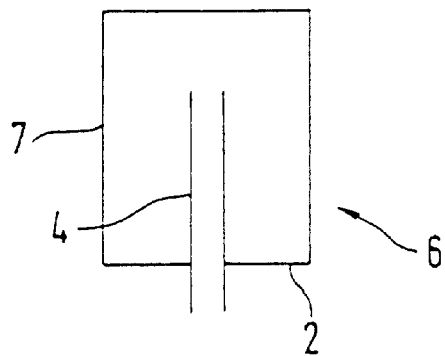
FIG. 2 shows a second pressure measuring apparatus with a measuring duct which is disposed internally in the container.

FIG. 2 shows a second pressure measuring apparatus 6 with a measuring duct 4 which is at least partially disposed in the interior of the container 2. In that way the pressure measuring apparatus becomes extremely compact and is even more comfortable to hold from the point of view of the operator. A contribution in that respect Is afforded by the fact that the container 2 has rigid walls 7 which can also be atomically matched to the gripping shape of a hand.

Figure 3:
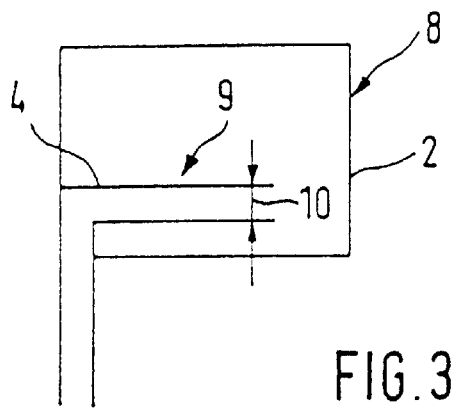
FIG. 3 shows a third pressure measuring apparatus with a horizontal measuring duct.

FIG. 3 shows a third pressure measuring apparatus 8 with a measuring duct 4 which is at least partially horizontally arranged. A horizontal portion 9 of the measuring duct 4 in the container 2 prevents falsification of the pressure measurement result as a result of the weight of blood itself or for example the common salt solution in the measuring duct 4. An advantageous maximum diameter 10 of the measuring duct 4 in the horizontal portion 9 is not more than 4 mm. That maximum diameter 10 is to be arranged in the usable measuring duct a, has is to say, where in a blood pressure measurement operation an indication in respect of the level of the blood in the measuring duct 4 or the common salt solution is also to be reckoned to occur.

Figure 4:
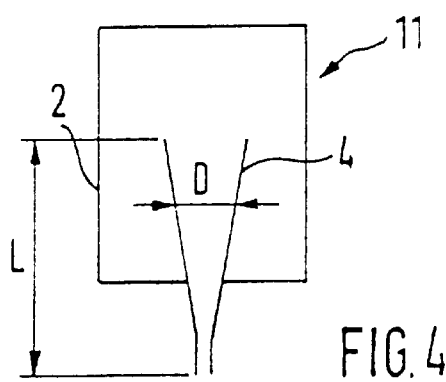
FIG. 4 shows a fourth pressure measuring apparatus with a continually enlarging measuring duct.

FIG. 4 shows a fourth pressure measuring apparatus 11. The measuring duct 4 continually increases in its diameter D along its length L. That permits accurate measurement of low pressure values at an upwardly large, open measuring scale, although there with a somewhat restricted degree of measuring accuracy. On the other hand a measuring duct 4 of that kind permits he container 2 to be of dimensions such that it can be held in a firm grip by a hand of the operator.

Figure 5:
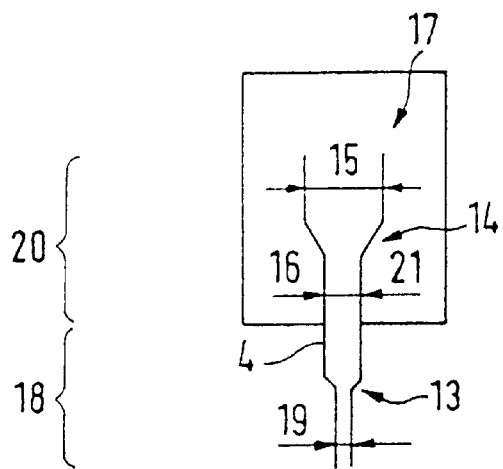
FIG. 5 shows a fifth pressure measuring apparatus with a stepped measuring duct.

FIG. 5 shows a fifth pressure measuring apparatus 12. The measuring duct 4 has a first stage 13 and a second stage 14. They are arranged in particular in such a way that, in the case of known pressure ranges and thus intervals between the blood pressure which is to be measured arterially and venously respectively, the container 2 can also be of a compact structure. For that purpose, a shape of the first stage 13 and the second stage 14 respectively can be conical, as illustrated, or however also in the shape of a staircase landing. Similarly to foregoing FIG. 4. FIG. 5 shows that a first diameter 15 of the measuring duct 4 is larger than a second diameter 16 of the measuring duct 4. The first diameter 15 is arranged in the container 2 closer to a mouth opening 17 of the measuring duct 4, than the second diameter 16. FIG. 5 further shows that a first portion 18 of the measuring duct 4 with a third diameter 19 is arranged outside the container 2 while a second portion 20 of the measuring duct 4 is disposed within the container 2, the third diameter 19 in the first portion 18 being smaller than a fourth diameter 21 of the measuring duct 4 in the second portion 20.

Figure 6:
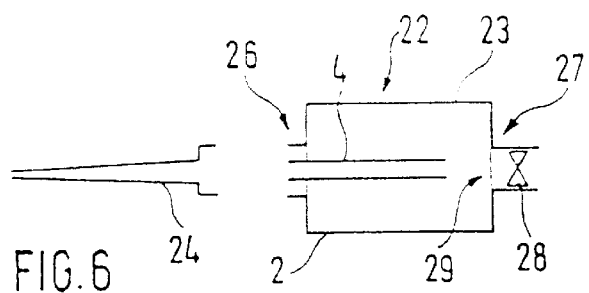
FIG. 6 shows a system with a sixth pressure measuring apparatus and a cannula.

FIG. 6 shows a first system 22 with a sixth pressure measuring apparatus 23 and a cannula 24. The cannula 24 can be connected to a cannula connection 26 on the sixth pressure measuring apparatus 23. The measuring duct 4 is arranged in the container 2 in such a way that the measuring duct 4 extends on the longitudinal axis of the connected cannula 24. The container 2 has an entry 27 which is preferably disposed in opposite relationship to the cannula connection 26 and which has a first valve 28 for closing an opening 29 of the container 2. The compressible medium in the container 2 is retained in the sixth pressure measuring apparatus 23 by the first valve 28. If a catheter (not shown here) is to be introduced into a blood vessel the correct position of the cannula 24 can firstly be reliably ascertained by means of pressure measurement. Subsequently a guide wire for a catheter or directly the catheter itself is introduced through the entry 27 and the opening 29 into the container 2 and then advanced into the blood vessel through the measuring duct 4 and the cannula 4.

Figure 7:
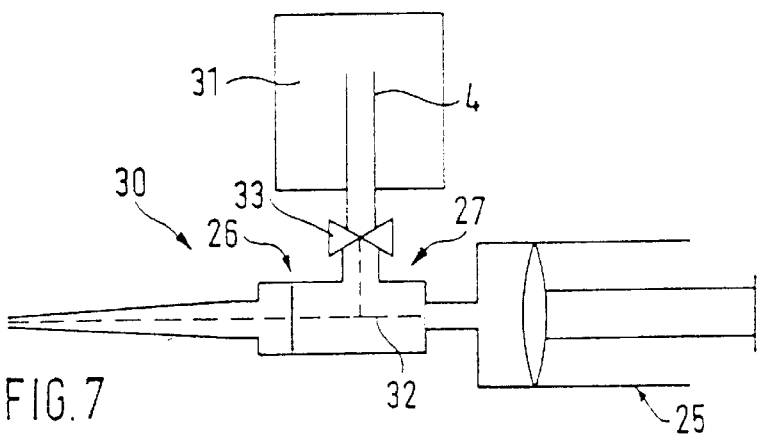
FIG. 7 shows a second system with a seventh pressure measuring apparatus and a cannula and a syringe.

FIG. 7 shows a second system 30. A seventh pressure measuring apparatus 31 has an integrated cannula connection 26 and an entry 27 for a syringe 25 which are connected together by way of a pressure line 32 which is indicated here in broken line. A part of the pressure line 32 is thus at the same time part of the measuring duct 4. A second valve 33 is in turn arranged in the measuring duct 4. If an aspiration operation is to be effected by means of the connected syringe 25 the second valve 33 can be closed and then opened again for the pressure measurement operation. In terms of its structure the second system 30 also permits the syringe to be substituted for a catheter. For that purpose for example provided in the pressure line 32 is a further valve (not shown here) with which the entry 27 can be closed. The second system 30, like the first system 22 of FIG. 6, also permits connection of the previously known "Raulerson syringe".

Figure 8:
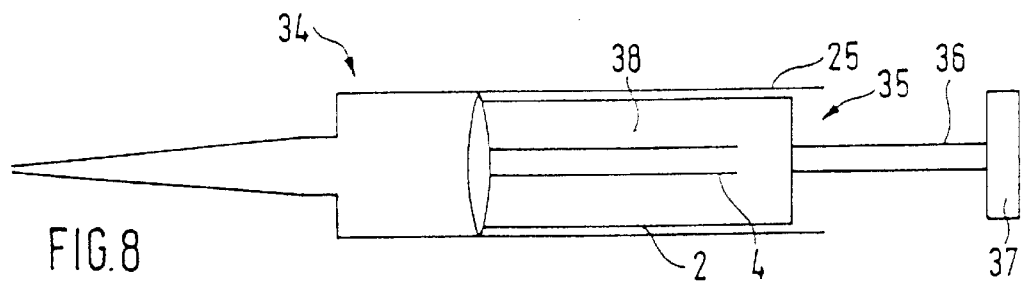
FIG. 8 shows a pressure measuring apparatus which is integrated into a syringe.

FIG. 8 shows a third system 34 in which the container 2 has been integrated into the syringe 25. The container 2 forms at least in part a plunger 35 of the syringe 25. The plunger 35 of the syringe 25 has a closable catheter passage 36. It is closed off relative to the exterior by a closure portion 37 at one side while the catheter passage 36 is opened at the other side to an internal space 38 of the container. In this case the closure portion 37 is integrated into the plunger 35. In another variant (not shown here) the closure portion can be fitted to the container and removed again. The measuring duct 4 in the container 2 again also serves as a catheter passage 36 after a pressure measurement operation has been effected.

Figure 9:
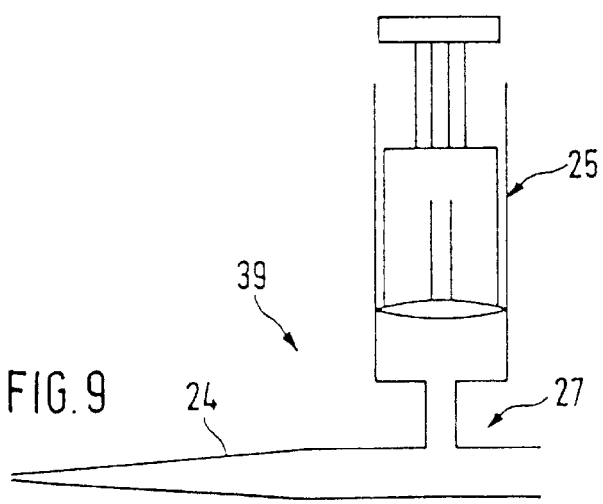
FIG. 9 shows a system comprising a pressure measuring apparatus integrated in a syringe, connected to a side-port cannula.

FIG. 9 shows a fourth system 39. The entry 27 which is preferably provided with a valve (not shown here) permits lateral connection of the syringe 25 or a sixth pressure measuring apparatus 23 to the cannula 24 (a so-called side-port cannula). In the case of the fourth system 39 a catheter can be introduced either directly through the cannula 24 or the fitted syringe 25 or the sixth pressure measuring apparatus 23.

Figure 10:
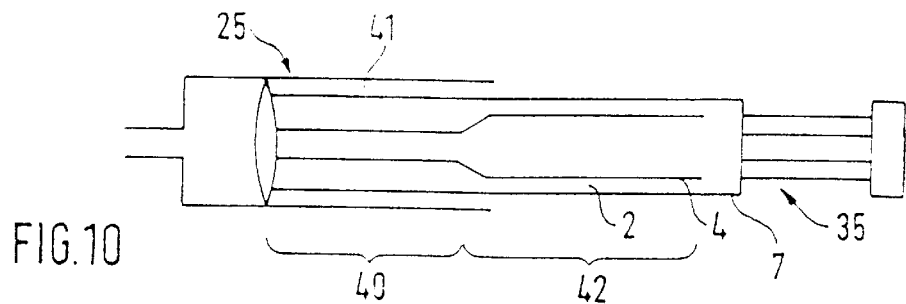
FIG. 10 shows a further syringe with integrated pressure measuring apparatus.

FIG. 10 shows a further variant of the design configuration of the measuring duct 4 disposed in the container 2 of the syringe 25 awhile a portion 40 of the measuring duct 4, which has a small lumen, is disposed within the syringe cylinder 41 for the predominant part in the movement of the plunger 35, a portion 42 of the measuring duct 4. which has a large lumen, is disposed outside the syringe cylinder 41, when the plunger 35 is fully pushed in, at least in regard to the predominant part thereof. The lumen of the measuring duct 4 in the small-lumen portion 40 can be optically enlarged by suitable material and suitable shaping of the measuring duct 4 in the container 2 or of the syringe cylinder 41. Low pressures measured in that small-lumen portion 40 of the measuring duct 4 can thus be accurately read off The large-lumen portion 42 of the measuring duct 4 is sized for the measurement of higher pressures over a greater range.

Figure 11:
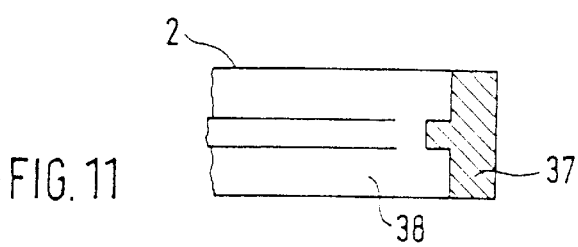
FIG. 11 shows, a container of the pressure measuring apparatus which is closed with a closure portion.

FIG. 11 shows a part of a possible design configuration of the container 2. The fitted closure portion 37 serves for closing and opening the internal space 38 in the container 2, for example for the introduction of a catheter (not shown here) through the measuring duct 4 into a bloodstream (also not shown).

Figure 12:
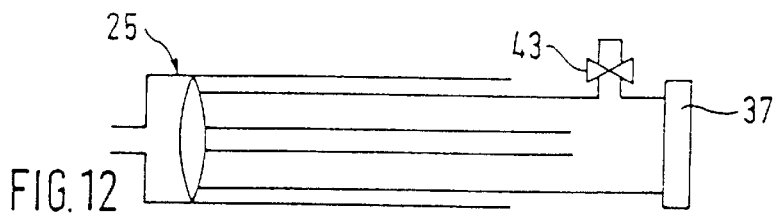
FIG. 12 shows a valve on a pressure measuring apparatus for venting the container.

FIG. 12 shows a further design configuration of the syringe 25. At one end it has a venting valve 43 for preparing the syringe 25 for the measurement of negative pressures. The venting valve 43 can also be arranged in the closure portion 37. Then, besides the venting function, it also takes over the function of affording a passage for a catheter.

Figure 13:
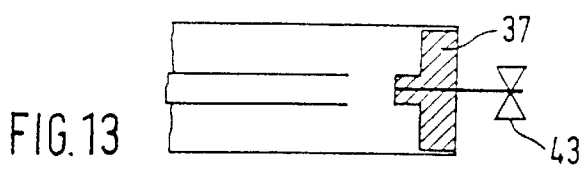
FIG. 13 shows a valve mounted on a closure portion for venting the container.

FIG. 13 shows a possible arrangement of the venting valve 43 which, as illustrated here, can be disposed on the closure portion 37 or however in the closure portion 37.

Figure 14:
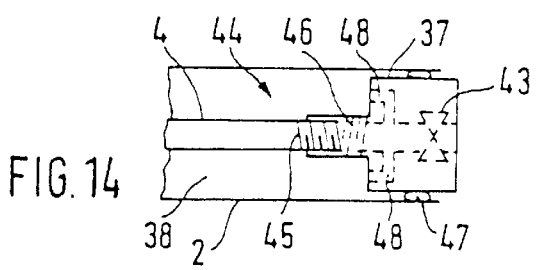
FIG. 14 shows a closure portion which is displaceable in the container.

FIG. 14 shows a further design configuration of the closure portion 37. It is displaceable in the container 2 in a controlled fashion, by means of the positioning means 44. For displacement purposes the measuring duct 4 has a male screwthread 45 and the closure portion 37 has in part a female screwthread 46. A seal 47 which is suitable for such displacement is disposed on the closure portion 37. As shown in broken lines, arranged in the closure portion 37 are a venting valve 43 and communicating ducts 48 which open into the internal space 38 in the container 2.

Figure 15:
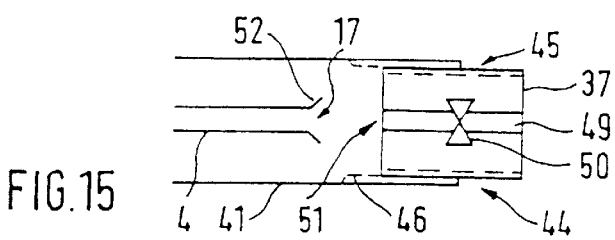
FIG. 15 shows a further displaceable closure portion.

FIG. 15 shows a further design configuration of the positioning means 44. The closure portion 37 with a closable passage 49 therethrough now has the male screwthread 45 while the syringe cylinder 41 has the female screwthread 46. The insertion of a catheter into the container 2 is again possible by way of a passage valve or straight-way valve 50 in the closure portion 37, a passage opening 51 in the closure portion 37 being disposed in directly opposite relationship to the mouth opening 17 of the measuring dun 4 into the container 2. in the container portion shown as part thereof, the measuring passage 4 also has a funnel portion 52. As the closure portion 37 regains spaced from the measuring duct 4 even in its end positions, the funnel portion 52 serves for the better introduction of a catheter into the measuring duct 4.

Figure 16:
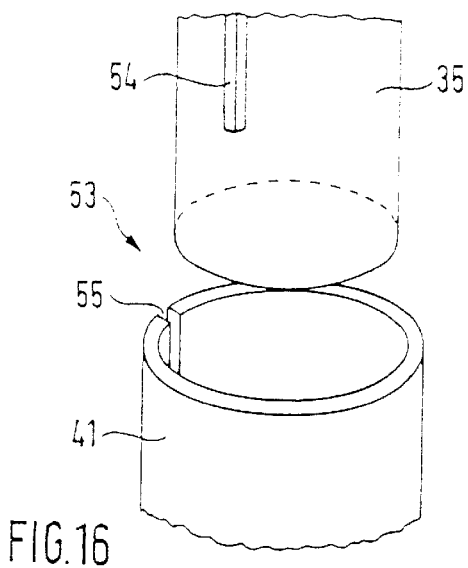
FIG. 16 shows a tongue-groove system as a press-in safeguard means.

FIG. 16 shows a press-in safeguard means 53 for a syringe (not shown) according to the invention. The plunger 35 and the syringe cylinder 41 have a tongue-groove system. It is only by rotating the plunger 35, as indicated by the arrow, that the tongue 54 and the groove 55 can be brought into alignment for the tongue 54 to be pushed Unto the groove 55. It is however also possible to use other mechanical systems as the press-in safeguard mean 53, such as obstacles or the like which have to be overcome by the application of a force, in the direction of pressing the plunger.

Figure 17:
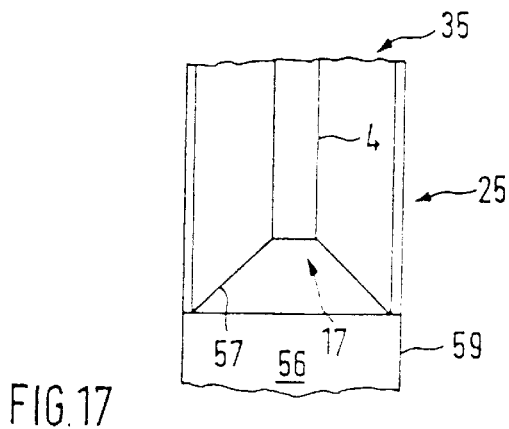
FIG. 17 shows a conical funnel shape of a bottom which faces towards a cylinder chamber of a syringe.

FIG. 17 shows a bottom or end portion 57 of the plunger 35 which faces towards a cylinder chamber 56 of the syringe 25 of which a part is shown. The end portion 57 which converges in a funnel-like configuration towards the mouth opening of the measuring duct 4 prevents an air bubble from becoming caught on the cylinder wall 59 in the cylinder chamber 56, as is to be observed in the case of an end portion 57 which extends perpendicularly relative to the measuring duct 4. In particular the end portion 57 can be of a concave shape.

FIG. 18 again shows a part of a configuration of the syringe 25. The container 2 is again integrated into the plunger 35. The measuring duct 4 is arranged eccentrically. A first seal 58 is arranged on the plunger 35 non-rotatably relative to the cylinder wall 59 of the syringe 25. Thus the first seal 58 follows the upward and downward movement of the plunger 35, while the plunger 35 itself remains rotatable within the first seal 58. The first seal 58 also has an orifice 60. The mouth opening 17 of the measuring duct 4 can be brought into alignment with the orifice 60 by rotary movement of the plunger. In that way blood or liquid can flow by way of the cylinder chamber 56 into the measuring object and thus blood pressure can be measured. A catheter can subsequently also be advanced out of the measuring duct 4 by way of the cylinder chamber 56.

Figure 18:
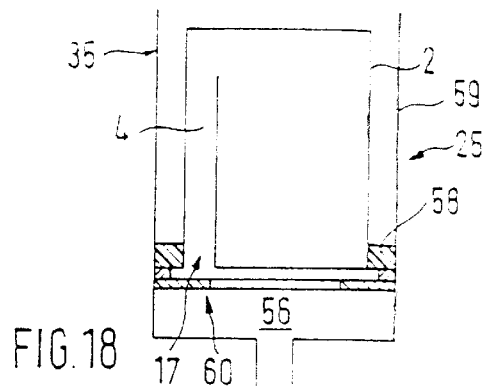
FIG. 18 shows an eccentrically arranged measuring duct in a syringe.
Figure 19:
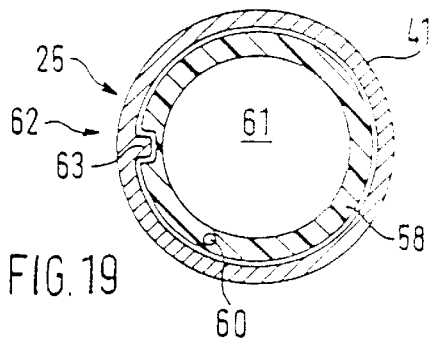
FIG. 19 is a view in cross-section through a syringe with integrate pressure measuring apparatus, wherein a seal is arranged non-rotatably with respect to the wall of the cylinder of the syringe.

FIG. 19 shows a view in cross-section through the first seal 58 and the syringe cylinder 41 of the syringe 25 of FIG. 18. A free inside surface 61 affords sufficient space for the plunger (not shown). As a rotary movement-preventing means 62 for preventing rotary movement of the first seal 58 the syringe cylinder 41 has a material thickening 63 to which the first seal 58 is adapted. The orifice 60 in the first seal 58 is so arranged that it can be opened or closed by rotation of the plunger (not shown). Besides such a rotary movement-preventing means 62, it is also possible to use other securing means which form part of the state of the art and which on the one hand permit the upward and downward movement of the plunger while on the other hand preventing the rotary movement of the first seal 58.

Figure 20:
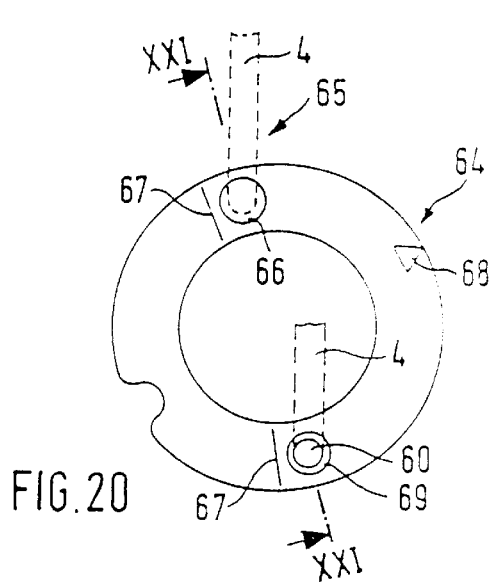
FIG. 20 is a plan view of a further seal corresponding to that illustrated in FIG. 19.

FIG. 20 shows a second seal 64 which is designed on the basis of the principle of the rotary movement-preventing means 62 of FIG. 19. The second seal 64 has a mouth closure 65. That mouth closure 65 is brought into engagement with the mouth opening of the measuring duct 4 and closed by rotation of the plunger (not shown). Advantageously, the mouth closure 65 is a dome-shaved raised portion 66. In addition, the seal 64 which is highly effective in this way affords a certain resistance upon rotation of the plunger as long as the mouth opening of the measuring duct 4 is closed. As a result that position is communicated to the operator by virtue of the higher level of torque which he has to apply. A further possible way of indicating the precise rotational position of the second seal 64 with respect to the plunger lies in a position indicating means 68 on the second seal 64 and a corresponding counterpart portion on the plunger (not shown here). In order to prevent the plunger from being over-rotated the second seal has two rotational abutments 67. The orifice 60 in turn is surrounded by a round bead or ridge 69 on the second seal 64. The measuring duct 4, illustrated in broken line, passes precisely into the centre of the bead or ridge 69, and is sealed off in that way. Moreover, the rotary abutment 67, for example in the form of a raised portion extending along the second seal 64, may also be a component of the mouth closure 65 or the orifice 60. The same applies in regard to the position indicating means 68 which in this case is arranged centrally between the mouth closure 65 and the orifice 60 on the second seal 64. For manufacturing reasons it may also be desirable for the plunger or also the cylinder wall to have a rotary abutment for the plunger, which acts either alone, in conjunction with other rotary abutments or the rotary abutments 67 on the second seal 64.

Figure 21:
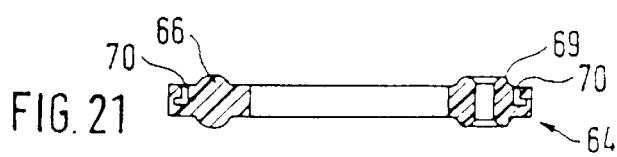
FIG. 21 is a view in cross-section through the seal of FIG. 20.

FIG. 21. a view in cross-section taken along line XXI—XXI in FIG. 20. shows that the dome-shaped raised portion 66, like the round bead or ridge 69, is part of the second seal 64. Entrainment of the plunger (not shown) in its upward and downward movement in the syringe cylinder is ensured by suitable free spaces 70 within the second seal 64. The plunger can engage, being of a suitable configuration, into those spaces 70 and can thus entrain the second Seal 64 therewith. The spaces 70 are of such a configuration that the plunger remains rotatable within the second seal 64. Alternatively the second seal 64 can also be designed in the form of a double seal which is then arranged rotatably in an annular groove in the plunger. That construction which 5s simpler from the manufacturing procedure point of view promises in particular even better sealing of the measuring duct 4.

Figure 22:
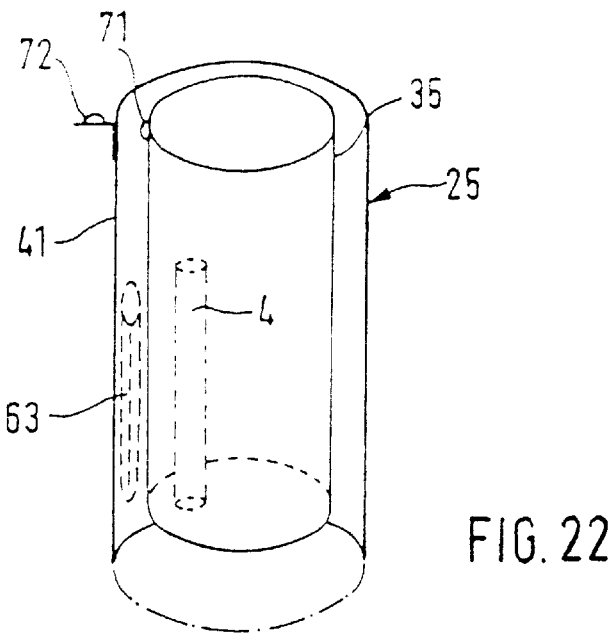
FIG. 22 is a diagrammatic view of a syringe with an eccentrically disposed measuring duct.

FIG. 22 is a diagrammatic view of a further configuration of the syringe 25. The syringe cylinder 41 again has a material thickening 63. It serves here on the one hand as a rotary movement-preventing means for the seal which is not shown in greater detail in FIG. 22. On the other hand it can be used as a magnifying lens for the measuring duct 4 which, in the opened position, that is to say during pressure measurement, is directly under the material thickening 63. In that way the pressure indication can be very clearly read off. At a mark 71 on the plunger 35 which can be for example touches by the operator of the syringe 25 at any time, it is possible to detect whether the measuring duct 4 is open or closed. If that mark 71 is disposed directly opposite a counterpart mark 72 which is disposed on the syringe cylinder and which for example can also be felt, then the measuring duct 4 is open.

Figure 23:
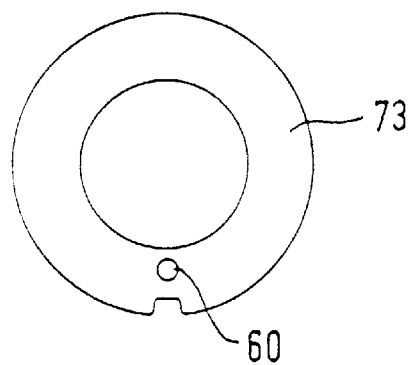
FIG. 23 shows a further seal which can be used for example in a syringe as shown in FIG. 22.

FIG. 23 shows the third seal 73 which is not shown in FIG. 22. In that case the orifice 60 is disposed precisely opposite the material thickening.

Figure 24:
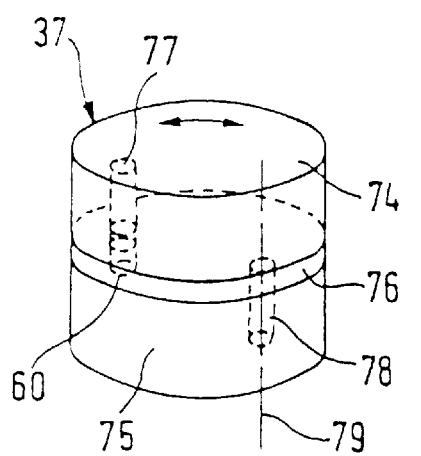
FIG. 24 shows a closure portion with a rotational part.

FIG. 24 shows a further configuration of the closure portion 37. The rotary part 74 is rotatably connected to a guide part 75 by way of an intermediate seal 76 which for example can have the sealing features described with reference to FIG. 21. In that way a first duct 77 in the rotary part 74, the orifice 60 in the intermediate seal 76 and a second duct 78 in the guide part 75 can be brought into alignment to form the passage 49 in the closure portion 47. The pressure measuring device which is closed rearwardly by the closure portion 37 can thus be vented or opened for the forward movement of a catheter. The passage 49 is indicated in broken line. Instead of the intermediate seal 76 with the orifice 60 it is also possible to use an intermediate seal without orifice, in which the orifice is first produced by being pierced through the material of the intermediate seal for example when a catheter is advanced. In the production of the closure portion 37 it is also possible from the outset to insert a material between the first duct 77 and the second duct 78, which material permits that subsequent production of the orifice 60.

FIG. 25 is again a diagrammatic view of a closure portion 37 which remains spaced from the measuring duct 4 in the plunger in any position. The gap 79 between the mouth opening 17 of the measuring duct 4 and the closure portion 37 prevents the discharge of blood or other liquids from the passage 49 indicated in broken line, and thus prevents the operator from suffering from contamination.

On the contrary the blood drips Into the container 2. In addition the closure portion 37 may have a drip surface 80 which is disposed opposite the mouth opening 17 of the measuring duct 4. The surface 80 is of such a design that, even in the event of an abrupt discharge of blood or other liquids from the mouth opening 17 of the measuring duct 4, for example due to inclined positioning of the drip surface 80, discharge from the passage 40 is still prevented even if it is open.

Figure 25:
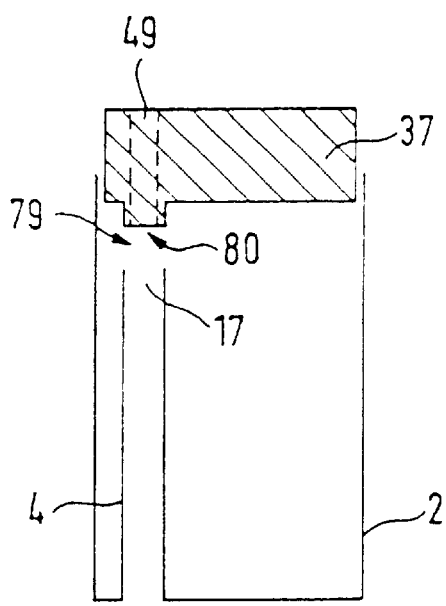
FIG. 25 shows a diagrammatic view of a container of a pressure measuring apparatus with spaced closure portion.
Figure 26:
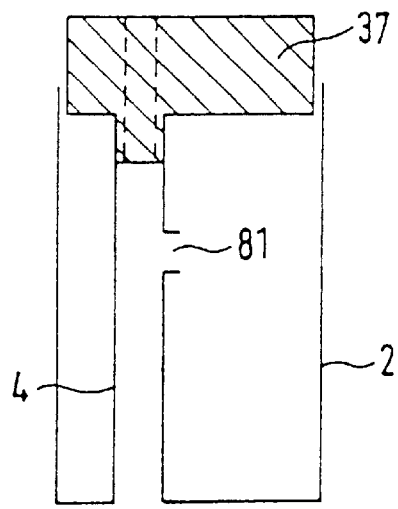
FIG. 26 shows a diagrammatic view of a container of a pressure measuring apparatus with inwardly displaced closure portion.

FIG. 26 snows an embodiment of the closure portion 37 and the measuring duct 4. which is different from that of FIG. 25. The measuring duct 4 additionally has a lateral opening 81 which opens to the container 2. The closure portion 37 fits onto the measuring duct 4 at the mouth opening 17. whereby forward movement of a catheter into the measuring duct 4 is facilitated. Nonetheless the function of pressure measurement is still retained by virtue of the opening 81. The opening 81 then serves as the mouth opening 17 of the measuring duct 4 into the container 2. The opening 81 of the measuring duct 4 can also be closed off by pushing in the closure portion 37 and in that way the measuring range of the pressure measuring device can be increased. It is also possible to provide on the measuring duct 4 a plurality of openings 81 from which blood or another liquid can possibly drip into the container 2.

Figure 27:
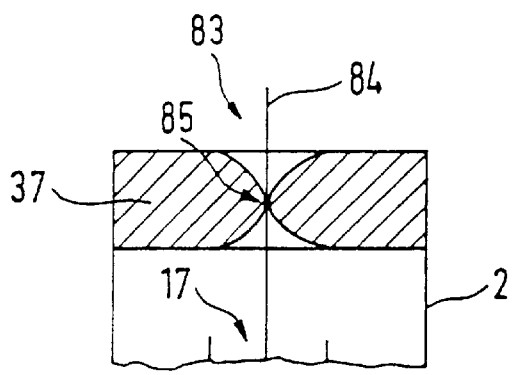
FIG. 27 shows a further diagrammatic view of a container of a pressure measuring apparatus with a sealing plug arranged in the measuring duct.
Figure 27:
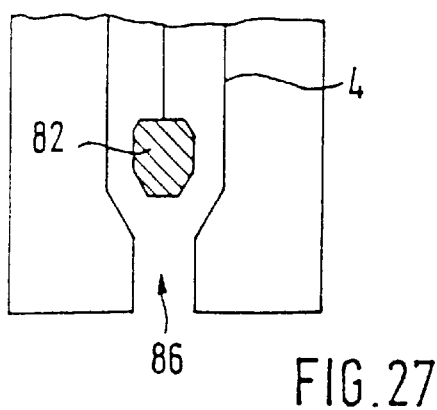
Figure 28:
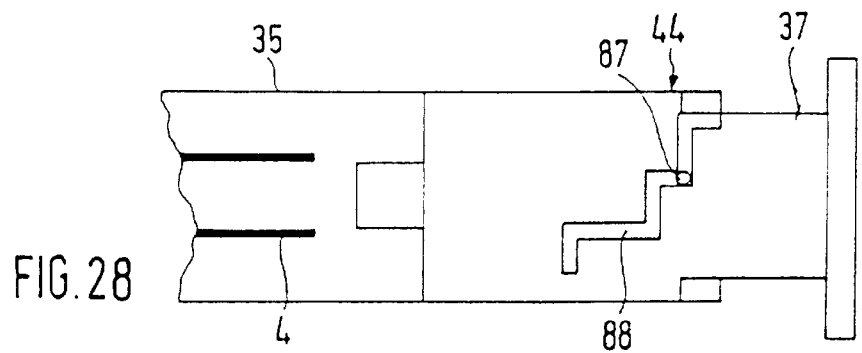
FIGS. 28 to 31 show a displaceable closure portion with positioning means.
Figure 29:
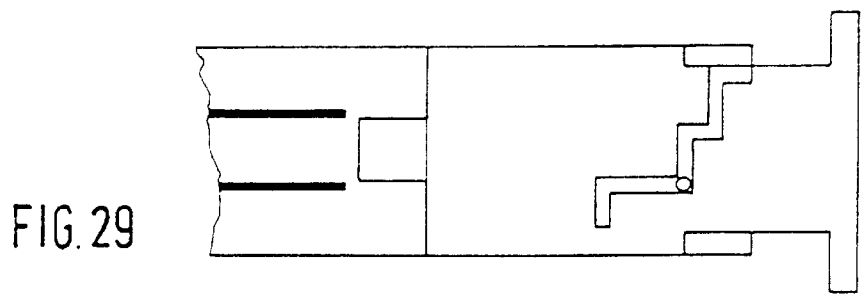
Figure 30:
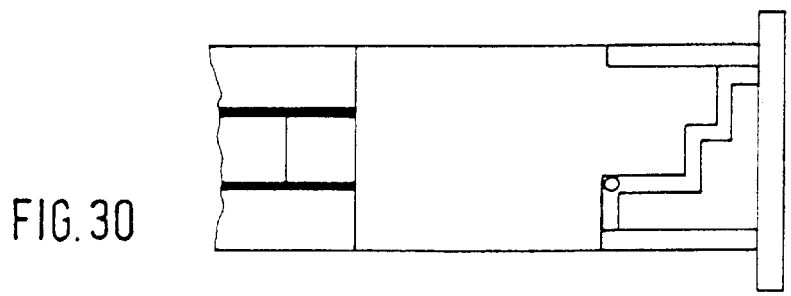
Figure 31:
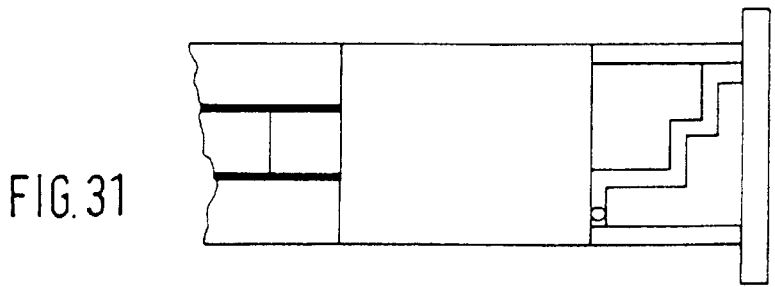

FIG. 27 shows a further embodiment of the measuring duct 4 and the closure portion 37. A displaceable sealing plug 82 is disposed in the measuring duct 4. The sealing plug 82 is movable upwardly and downwardly in the measuring duct 4 by means of a guide 83, in this case a wire 84. from outside the container 2. The associated closure portion 37 has a fourth seal 85 which permits the sealing plug 82 to be removed. At the same time the fourth seal 85 is so designed that re-introduction of the sealing plug 82 or for example a catheter is also possible. The sealing plug 82 is again of such a shape that it fits into a constriction 86 in the measuring duct 4 or in the pressure line (not shown here), fills it up and seals it off. In that way it is possible for the measuring duct 4 to be opened only for the pressure measurement operation and possibly closed again after pressure measurement has been implemented, for example for the further aspiration of blood, without the sealing plug 82 being completely pulled out of the container 2 in that procedure. Blood pressure measurement can thereby be interrupted and in particular repeated. After the interruptions it is possible for example to effect equalisation or balancing operations. The constriction 86 is arranged closer to the cannula connection (not shown) than to the mouth opening 17 of the measuring duct 4 into the container 2.

FIGS. 28, 29, 30 and 31 show a further configuration of the closure portion 37 with a suitable positioning means 44. The passage for the closure portion 37 is not illustrated in this case. The closure portion 37 can be displaced by way of a pin 87 along a step-like aperture 88 in the plunger 35 until the measuring duct 4 is closed. The step-like aperture 88 defines different displacement positions of the closure portion 37, in which the closure portion 37 is secured to prevent it from unintentionally slipping back, for example in the event of pressure in the plunger. Due to the step-wise inward movement of the closure portion 37, the pressure measuring device can be prepared in defined steps for the measurement of higher pressures, whereas by virtue of the step-wise retraction movement of the closure portion 37 it can be prepared for the measurement of low and even negative pressures.

The invention describes the concept of a simple, compact, easily understandable, sufficiently accurate one-trip or disposable manometer which can be easily sterilised, preferably in the form of a syringe, with which cavities for example in the human body can be differentiated or identified on the basis of the pressure involved, and by means of which, with a suitable structure, guide wires for catheters or catheters can be inserted into cavities for example in the human body, without contamination of the working area.

The possibility of measuring the blood pressure in veins and arteries even through cannulae having a small lumen and thus being able to distinguish the vessels reduces the risk of an arterial mis-puncture with large-lumen cannula, which is potentially dangerous for the patient, and minimises the risk of unintentional catheter insertions into arteries or the non-recognition of incorrect arterial catheter positions. Severe bleeding complications resulting from such incorrect positioning and surgical interventions involving blood vessels, which are necessary as a result, are avoided.

As unintentional puncturing of an artery in the neck with a large-lumen cannula or the insertion of a large-lumen catheter can result in the mobilisation of arteriosclerotic plaques and entrainment of that material into arteries supplying the brain with the consequence of a stroke, the medico-legal significance of this concept is apparent: the invention as set out hereinbefore defines a new state of the art. Managing without this simple, rapid and comparatively inexpensive possibility of blood pressure-monitored insertion of central-venous catheters can have consequences from the point of view of legal liability—not only from the point of view of the doctor who incurs a higher puncturing risk and involves a complication, but possibly also for a company which offers central-venous catheters. Thus it is possible to envisage a lower premium in respect of product liability insurance for a central-venous catheter which is sold for example with a "manometer syringe".

In terms of the cost-profit calculation the costs of a disability as a consequence of a stroke must be compared to the costs of the use of such a syringe, in consideration of the catastrophic consequence for the person affected. However this concept proves its worth not only from the point of view of economy but also in terms of operational efficiency due to a time saving (faster checking in comparison with implementing a blood gas analysis operation) and a cost saving (an incorrectly disposed catheter has to be pulled out and a fresh one fitted).

In contrast to the connection of a conventional pressure-detection system for pressure monitoring, which is not prepared in a sterile condition, satisfactory sterile operation is possible even without an assistant. A closed system also has hygiene advantages, in comparison with a hose which is open lo the pressure of the atmosphere.

Like also the "Enk syringe" the structures described herein are also suitable for the continuous "blood" measurement of the arterial (mean) pressure, for example in the context of accident and emergency medicine, for monitoring the central-venous (mean) pressure or also for measuring the pressure of cerebrospinal fluid.

The syringe described in various configurations does not necessarily require precision manufacture and in principle can already be made up from five parts. By virtue of a sufficiently large volume of air in the plunger and depending on the relationship of the volume of the measuring duct and the cavity in the plunger, it is possible to design or optimise the syringe according to requirements for given pressure measuring ranges. In that respect it is only necessary for the friction of the sealing lip of the plunger to be sufficiently high to hold the plunger in its position in the syringe cylinder even when the injecting finger completely relieves its pressure on the plunger.

List of References 1 first blood pressure measuring apparatus
2 container
3 compressible medium
4 measuring duct
5 common salt solution
6 second blood pressure measuring apparatus
7 rigid wall
8 third blood pressure measuring apparatus
9 horizontal portion
10 maximum diameter
11 fourth blood pressure measuring apparatus
12 fifth blood pressure measuring apparatus
13 first stage
14 second stage
15 first diameter
16 second diameter
17 mouth opening
18 first portion
19 third diameter
20 second portion
21 fourth diameter
22 first system
23 sixth blood pressure measuring apparatus
24 cannula
25 syringe
26 cannula connection
27 entry
28 first valve
29 opening
30 second system
31 seventh blood pressure measuring apparatus
32 pressure line
33 second valve
34 third system
35 plunger
36 catheter passage
37 closure portion
38 internal space in the container
39 fourth system
40 small-lumen portion
41 syringe cylinder
42 large-lumen portion
43 venting valve
44 positioning means
45 male screwthread
46 female screwthread
47 seal
48 communicating duct
49 passage
50 passage valve
51 passage opening
52 funnel portion
53 press-in safeguard means
54 tongue
55 groove
56 cylinder chamber
57 end portion
58 first seal
59 cylinder wall
60 orifice
61 free inside surface
62 rotary movement-preventing means
63 material thickening
64 second seal
65 mouth opening closure
66 dome-shaped raised portion
67 rotary abutment
68 position indication means
69 round bead
70 free space
71 mark
72 counterpart mark
73 third seal
74 rotary part
75 guide part
76 intermediate seal
77 first duct
78 second duct
79 gap
80 drip surface
81 aperture
82 sealing plug
83 guide
84 wire
85 fourth seal
86 constriction
87 pin
88 step-like opening
D diameter
L length

I claim:
1. A one-person-operable, sterilisable, medical pressure measuring apparatus, comprising:
a closed container with rigid walls and an entry, said closed container having a compressible medium therein;
at least one cannula connection for connecting at least one cannula to said closed container; and
a measuring duct with a mouth opening into said closed container, said measuring duct having a first diameter and a second diameter, said first diameter being larger than said second diameter, said first diameter being disposed closer to said mouth opening than said second diameter.

2. A one-person-operable, sterilisable, medical pressure measuring apparatus, comprising:
a closed container with rigid walls and an entry, said closed container having a compressible medium therein;
at least one cannula connection for connecting at least one cannula to said closed container; and
a measuring duct opening into said closed container, said measuring duct having a first portion with a first diameter disposed outside said container and a second portion with a second diameter disposed within said container, said first diameter being smaller than said second diameter.

3. A one-person-operable, sterilisable, medical pressure measuring apparatus, comprising:
a closed container with rigid walls and an entry, said closed container having a compressible medium therein;
at least one cannula connection for connecting at least one cannula to said closed container; and
a measuring duct opening into said closed container, said measuring duct having a diameter changing over a length of said measuring duct.

4. The pressure measuring apparatus according to claim 3, wherein said measuring duct is disposed one of in and outside said container.

5. The pressure measuring apparatus according to claim 3, wherein said at least one cannula connection permits lateral connection of a cannula.

6. The pressure measuring apparatus according to claim 5, wherein in a connected condition of the cannula said measuring duct extends on a longitudinal axis of the cannula.

7. The pressure measuring apparatus according to claim 5, wherein in a connected condition of the cannula said measuring duct extends at an angle to the cannula.

8. The pressure measuring apparatus according to claim 7, wherein in the connected condition of the cannula said measuring duct extends perpendicularly to the cannula.

9. The pressure measuring apparatus according to claim 3, wherein a maximum diameter of said measuring duct is no greater than 5 millimeters.

10. The pressure measuring apparatus according to claim 9, wherein said maximum diameter of said measuring duct is no greater than 4 millimeters.

11. The pressure measuring apparatus according to claim 3, wherein said measuring duct is disposed eccentrically in said container.

12. The pressure measuring apparatus according to claim 3, wherein said container has a first valve for an internal space of said container.

13. The pressure measuring apparatus according to claim 12, wherein said first valve is a venting valve.

14. The pressure measuring apparatus according to claim 12, wherein said measuring duct has a second valve.

15. The pressure measuring apparatus according to claim 3, including at least one cannula connected to said at least one cannula connection.

16. The pressure measuring apparatus according to claim 3, wherein a displaceable sealing plug is disposed in said measuring duct, said sealing plug is movable in said measuring duct by a guide from outside said container.

17. The pressure measuring apparatus according to claim 16, including a pressure line, one of said measuring duct and said pressure line has a constriction, said sealing plug fills and seals off said construction.

18. The pressure measuring apparatus according to claim 17, wherein said constriction is disposed closer to said cannula connection than to said mouth opening of said measuring duct.

19. A one-person-operable, sterilisable, medical pressure measuring apparatus, comprising:
a closed container with rigid walls and a closable opening into an internal space in said container, said closed container having a compressible medium therein;
at least one cannula connection for connecting at least one cannula to said closed container; and
a measuring duct with a mouth opening into said closed container, said mouth opening being disposed in directly opposite relationship to said closable opening of said container.

20. The pressure measuring apparatus according to claim 19, wherein said container has a closure portion which can be inserted and removed again.

21. The pressure measuring apparatus according to claim 20, wherein said closure portion is controllably displaceable in said container by a positioning device.

22. The pressure measuring apparatus according to claim 20, wherein said closure portion has a passage.

23. The pressure measuring apparatus according to claim 22, wherein a straight-way valve is disposed in said passage.

24. The pressure measuring apparatus according to claim 22, wherein said closure portion has a rotational part which upon rotating opens or closes said passage.

25. The pressure measuring apparatus according to claim 20, wherein said closure portion has a passage opening in directly opposite relationship to said mouth opening of said measuring duct.

26. The pressure measuring apparatus according to claim 20, wherein said closure portion is spaced from said measuring duct.

27. The pressure measuring apparatus according to claim 19, wherein said measuring duct has laterally along the length thereof at least one opening which opens into said container.

28. The pressure measuring apparatus according to claim 27, wherein said at least one opening is a mouth opening of said measuring duct into said container.

29. The pressure measuring apparatus according to claim 28, wherein said measuring duct can be closed by a closure portion.

30. The pressure measuring apparatus according to claim 29, wherein said closure portion is one of rotatable and slidable, said measuring duct can be closed and opened again.

31. A one-person-operable, sterilisable, medical pressure measuring apparatus, comprising:
a closed container with rigid walls, said closed container having a compressible medium therein, said container being integrated into a plunger of a syringe, said syringe having a closable catheter passage which extends through said plunger of said syringe;
at least one cannula connection for connecting at least one cannula to said closed container; and
a measuring duct opening into said closed container.

32. The pressure measuring apparatus according to claim 31, wherein said measuring duct at least in part forms said catheter passage.

33. The pressure measuring apparatus according to claim 31, wherein said plunger has a press-in safeguard device.

34. The pressure measuring apparatus according to claim 33, wherein said plunger and a syringe cylinder have a tongue-groove system, wherein it is only by rotation of said plunger that a tongue and a groove are to be brought into alignment for insertion of said tongue into said groove.

35. The pressure measuring apparatus according to claim 31, wherein an end portion of said plunger, which is towards a cylinder chamber of said syringe, is of a funnel shape which converges towards a mouth opening of said measuring duct.

36. The pressure measuring apparatus according to claim 35, wherein said end portion is concavely curved.

37. The pressure measuring apparatus according to claim 31, wherein a seal is disposed on said plunger, said seal is disposed non-rotatably with respect to a cylinder wall of said syringe and has an orifice which by rotation of said plunger can be brought into alignment with a mouth opening of said measuring duct.

38. The pressure measuring apparatus according to claim 37, wherein said cylinder wall has a material thickening as a rotary movement-preventing device for said seal and said measuring duct lies in an opened position in a nearest position to said material thickening.

39. The pressure measuring apparatus according to claim 37, wherein said seal has a mouth closure which by rotation of said plunger can be brought into engagement with a mouth opening of said measuring duct.

40. The pressure measuring apparatus according to claim 39, wherein said mouth closure is a dome-shaped raised portion on said seal.

41. The pressure measuring apparatus according to claim 37, wherein at least one of said plunger, said seal and said cylinder wall has a rotary abutment for said plunger.

* * * * *